United States Patent
Badejo et al.

(10) Patent No.: US 6,420,590 B1
(45) Date of Patent: Jul. 16, 2002

(54) CONTINUOUS PROCESSES AND APPARATUS FOR FORMING CYANOACETATE AND CYANOACRYLATE

(75) Inventors: Ibraheem T. Badejo, Morrisville; Jaime Ayarza; Kenneth W. Davis, both of Raleigh; Jeffrey R. Hennenkamp, Wake Forest, all of NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/699,508

(22) Filed: Oct. 31, 2000

(51) Int. Cl.[7] .................. C07C 255/23; C07C 255/30
(52) U.S. Cl. .................. 558/443; 558/381; 558/375
(58) Field of Search ................... 558/443, 381, 558/375

(56) References Cited

U.S. PATENT DOCUMENTS

| | | | |
|---|---|---|---|
| 2,467,927 A | 4/1949 | Ardis et al. | 260/465.4 |
| 2,721,858 A | 10/1955 | Joyner et al. | 260/67 |
| 3,728,373 A | 4/1973 | Imohel et al. | 260/465 |
| 4,986,884 A | 1/1991 | Arlt et al. | 558/443 |
| 5,436,363 A | 7/1995 | Wang et al. | 558/381 |
| 5,624,669 A | 4/1997 | Leung et al. | 424/78.35 |
| 5,698,730 A | 12/1997 | Nakamura et al. | 558/443 |
| 5,928,611 A | 7/1999 | Leung | 422/131 |
| 5,981,621 A | 11/1999 | Clark et al. | 523/118 |

FOREIGN PATENT DOCUMENTS

JP 10-95760 4/1998

*Primary Examiner*—Floyd D. Higel
*Assistant Examiner*—Ebenezer Sackey
(74) *Attorney, Agent, or Firm*—Oliff & Berridge, PLC

(57) ABSTRACT

Continuous processes for forming cyanoacrylate from polycyanoacrylate include stripping a solvent from a reaction mass; cracking a polymer in the reaction mass to form a cracked cyanoacrylate monomer and residue substances; and distilling the cracked cyanoacrylate monomer to produce a cyanoacrylate monomer product. These steps can be performed in short-path, wiped-film evaporators. Polycyanoacrylate used in the processes can be formed using cyanoacetate produced by processes for continuously producing cyanoacetate by forming a higher homologue cyanoacetate from a lower homologue cyanoacetate. The cyanoacetate can be formed in short-path, wiped-film evaporators.

28 Claims, 4 Drawing Sheets

CONTINUOUS PROCESSES AND APPARATUS FOR FORMING CYANOACETATE AND CYANOACRYLATE

BACKGROUND OF THE INVENTION

1. Field of Invention

This invention relates to processes and apparatus for forming cyanoacetate and cyanoacrylate.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of these monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Cyanoacrylate monomers are generally produced by forming polycyanoacrylate and then cracking the polycyanoacrylate polymer to produce monomeric cyanoacrylate. Polycyanoacrylate is commonly produced by first reacting cyanoacetate with formaldehyde, or a functional equivalent such as the polymeric form paraformaldehyde, in the presence of a base. The base acts as a catalyst for the reaction between the cyanoacetate and paraformaldehyde. This reaction in the presence of the catalyst produces formaldehyde and polycyanoacrylate.

An exemplary known process for forming cyanoacetate is described in Japanese Patent Appln. Laid Open No. 60-95760. The disclosed process synthesizes cyanoacetate in a wiped-film evaporator using dibutyltin oxide. Titanium tetraisopropoxide can be used as a catalyst. A continuous process is disclosed.

A method for preparing cyanoacetic acid higher ester is described in U.S. Pat. No. 5,698,730 to Nakamura et al. This method includes subjecting a cyanoacetic acid ester to a transesterification reaction in the presence of a tin compound.

These known methods for producing cyanoacetate do not convert a lower homologue cyanoacetate to a higher homologue cyanoacetate in a continuous process.

Known processes for cracking polycyanoacrylate to produce cyanoacrylate monomer have many disadvantages. One disadvantage of the known processes is that they produce unwanted byproducts that must be separated from the monomer product. Such byproducts include, for example, alcohols and cyanoacetate. Often it is difficult and/or costly to remove such byproducts from the monomer product, resulting in impure product, increased production cost and time, and/or reduced yield. In addition, such impure product may not be suitable for certain uses, such as, for example, animal and human use.

Another disadvantage of known processes for cracking polycyanoacrylate is that during the cracking process, the temperature of the polycyanoacrylate is not sufficiently controlled to avoid the formation of what is referred to as "hot monomer." If the polymerization temperature is too high, monomer tends to polymerize on surfaces of the reactor, causing a buildup in the reactor. In addition, if the polycyanoacrylate polymer is cracked at too high of a temperature, the resulting monomer may not be stable. This problem again can result in an impure product, increased production cost and time, and/or decreased yield.

Further, in known processes of cracking polycyanoacrylate, the entire polymer is exposed to a high temperature for a long period of time, typically for as long as about eight hours or more. Consequently, side products are also formed during cracking. Hot monomers can form, which are overly reactive and have a tendency to polymerize. Consequently, such hot monomers have an insufficiently short shelf life.

U.S. Pat. No. 3,728,373 to Imohel et al. discloses a method for producing cyanoacrylic acid esters by depolymerizing polycyanoacrylic acid esters in a continuous process. In this process, polymer is admixed with an inert liquid having a high boiling point and a polymerization inhibitor. Depolymerization is conducted in a reaction zone at a temperature of 150–250° C. and a vacuum pressure of 0.5–40 mm Hg. Wiper blades in the reaction zone distribute the mixture in the form of a thin film having a thickness of up to 5 cm. Cyanoacrylic acid esters that are released from the reaction zone are passed to a condenser and collected in receivers. A dispersion of polycyanoacrylic acid esters and other components is collected as a thin layer on the surface of Woods metal filled in a vessel. The temperature of the metal surface is 180–240° C. in the vessel. Vapors of the monomeric cyanoacrylic acid ester are condensed in a cooled receiver.

U.S. Pat. No. 4,986,884 to Arlt et al. discloses a process for the production of monomeric α-cyanoacrylates. The Arlt process produces monomeric cyanoacrylates by pyrolyzing poly-α-cyanoacrylates. The monomer is subsequently distilled in a distillation column. The distillation is carried out in a counter current apparatus at reduced pressure over a plurality of separation stages. Polymerization inhibitors are fed continuously to the counter current at an uppermost separation stage. Liquid monomer is fed in at places where the condensation can collect in the apparatus.

U.S. Pat. No. 5,436,363 to Wang et al. discloses a method for making cyanoacrylate by the depolymerization of poly (alkyl-α-cyanoacrylate). In the Wang process, a reaction mixture containing poly(alkyl-α-cyanoacrylate), a polymerization inhibitor and a solvent is fed into a film evaporator to depolymerize the feed material. The film evaporator is operated at a pressure of 10 mm Hg vacuum and a temperature of about 200°–260° C. A first gas stream and a first residual liquid stream are produced from the film evaporator. The first residual liquid stream is passed to a collector. The first gas stream is fed to an intermediate heat exchanger having a very high temperature of about 150° C. to produce a second gas stream and a second residual stream of high-boiling residue. The second gas stream is fed from a liquid collector to a second heat exchanger (condenser) to form alkyl-α-cyanoacrylate monomer.

Wang utilizes classical wiped-film evaporator technology. However, such wiped-film devices cannot operate at low pressure levels, such as at micron pressure levels, i.e., pressures as low as about $10^{-3}$ mbar. Consequently, wiped-film evaporators heat the polymer to a relatively high temperature. As explained above, however, heating the polymer to high temperatures is disadvantageous, as it produces hot monomers and unwanted byproducts.

Thus, there is a need for a process that can produce cyanoacrylate monomer from polycyanoacrylate without incurring the above-described disadvantages of known processes. There is also a need for a continuous process for preparing cyanoacetate that converts a lower homologue cyanoacetate to a higher homologue cyanoacetate.

SUMMARY OF THE INVENTION

This invention provides processes and apparatus for the production of cyanoacrylate from polycyanoacrylate that satisfy one or more of the above-described needs.

Processes and apparatus for producing cyanoacrylate according to this invention can produce cyanoacrylate in a continuous manner. The cyanoacrylates that can be produced include alkyl cyanoacrylates, as well as other types of cyanoacrylates.

In addition, processes and apparatus for producing cyanoacrylate according to this invention can reduce exposure of polycyanoacrylate to high temperatures. Consequently, the above-described problems associated with exposing polycyanoacrylate to high temperatures, that occur in known processes and apparatus for forming cyanoacrylate, can be avoided.

Embodiments of this invention can produce cyanoacrylate with reduced waste, increased efficiency and at reduced cost.

This invention also provides processes and apparatus for the continuous production of cyanoacetate. Embodiments of the processes can convert a lower homologue cyanoacetate to a higher homologue cyanoacetate. The cyanoacetate produced by these processes can subsequently be used in embodiments of the above-described processes for continuously producing cyanoacrylate according to this invention.

BRIEF DESCRIPTION OF THE DRAWINGS

Preferred embodiments of this invention will be described in detail, with reference to the following figures, in which.

DETAILED DESCRIPTION OF PREFERRED EMBODIMENTS

Figure 2:
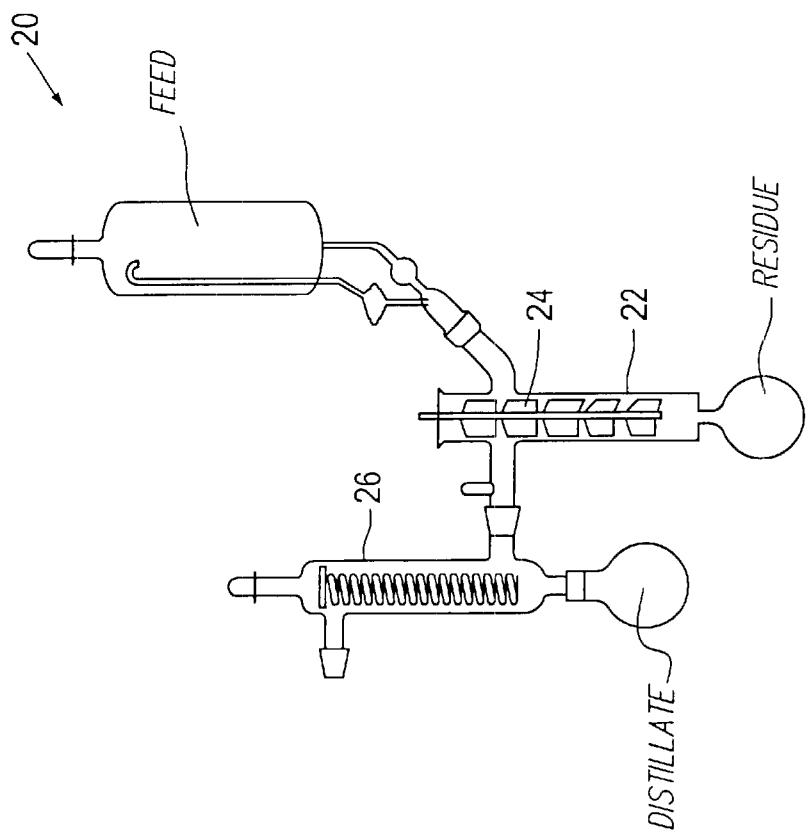
FIG. 2 illustrates a classical wiped-film evaporator.

This invention provides processes and apparatus for producing cyanoacrylate from polycyanoacrylate. Embodiments of the invention produce cyanoacrylate in a continuous manner. Embodiments of processes and apparatus for producing cyanoacrylate according to this invention use one or more wiped-film evaporators such as those shown in FIGS. 1 and 2 and, preferably, one or more short-path, wiped-film evaporators, such as that shown in FIG. 1.

This invention further provides processes for continuously producing cyanoacetate. The cyanoacetate produced in processes according to this invention can be utilized in processes of the invention for producing cyanoacrylate. Thus, for example, the cyanoacetate produced according to processes of this invention can be fed directly into a cyanoacrylate production process, including embodiments of the processes of producing cyanoacrylate according to this invention, to provide a combined continuous process of producing both cyanoacetate and cyanoacrylate. Alternatively, cyanoacetates produced by processes according to this invention can be stored for later use and/or used in other processes.

Embodiments of processes for forming cyanoacetate according to this invention can utilize one or more wiped-film evaporators and, preferably, one or more short-pass, wiped film evaporators.

Embodiments of processes for continuously producing cyanoacrylate from polycyanoacrylate according to this invention comprise stripping a solvent from a reaction mass produced from a synthesis step and cracking polymer contained in the reaction mass to form a distillate comprising cracked cyanoacrylate monomer and residue substances. The cracked cyanoacrylate monomer is distilled to produce a purified cyanoacrylate monomer.

In embodiments of processes according to this invention, the cracked cyanoacrylate monomer can be distilled twice. Particularly, the distillate can be distilled a first time to separate the volatile substances from the cracked cyanoacrylate monomer. The cracked cyanoacrylate monomer can then be distilled a second time to produce purified cyanoacrylate monomer product.

In embodiments of processes for continuously producing cyanoacrylate from polycyanoacrylate according to this invention, one or more wiped-film evaporators are used to perform different process steps. Particularly, a wiped-film evaporator is preferably used for stripping solvent from the reaction mass. The same or a different wiped-film evaporator is also used to crack the polymer in the reaction mass to form a cracked cyanoacrylate monomer and residue substances.

In embodiments, wiped-film evaporators are also used for distilling the cracked cyanoacrylate monomer. For example, a wiped-film evaporator can be used to separate the volatile substances from the cracked cyanoacrylate monomer. The same or a different wiped-film evaporator as used in the first distillation step can then be used to distill the cracked cyanoacrylate monomer again to produce purified cyanoacrylate monomer product.

Wiped-film evaporators used in processes for continuously producing cyanoacrylate from polycyanoacrylate according to this invention are preferably short-path, wiped-film evaporators. A suitable short-path, wiped-film evaporator for use in processes of this invention includes, but is not limited to, the Model KDT-4 evaporator, available from UIC Incorporated of Joliet, Ill. Other short-path, wiped-film evaporators, including wiped-film evaporators of different sizes and/or configurations, can also be used in embodiments of this invention.

Figure 1:
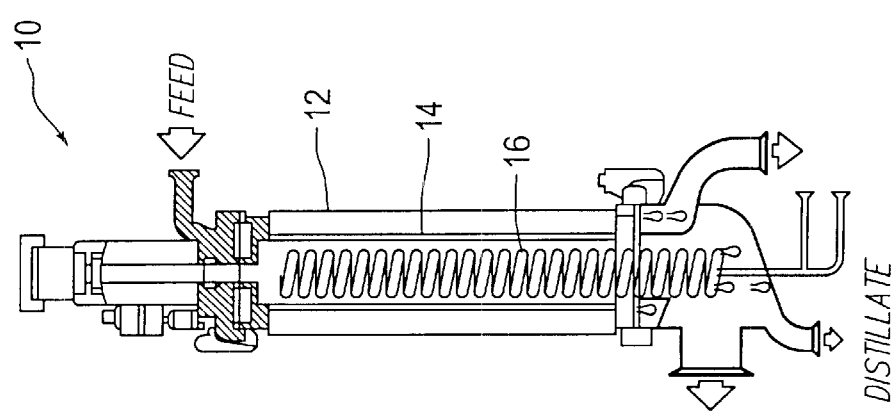
FIG. 1 illustrates a short-path, wiped film evaporator.

Embodiments of the processes and apparatus utilize short-path, wiped-film evaporators. Short-path, wiped-film evaporators provide important advantages as compared to classical wiped-film evaporators (referred to hereinafter as "wiped-film evaporators") that have been used in known processes. FIG. 1 illustrates an exemplary short-path, wiped-film evaporator 10. The short-path, wiped-film evaporator 10 includes a heating surface 12, a wiper system 14 and an internal condenser 16. FIG. 2 illustrates an exemplary wiped-film evaporator 20. The wiped-film evaporator 20 includes an evaporator 22 including wiper blades 24, a condenser 26 and a conduit connecting the evaporator 22 and condenser 26. In contrast to the short-pass, wiped-film evaporator 10, in the wiped-film evaporator 20, the condenser 26 is external to the evaporator system.

The difference in location of the internal condenser 16 in the short-pass, wiped-film evaporator 10 as compared to the external condenser 26 in the wiped-film evaporator 20 significantly affects the operation of these two evaporators. That is, in evaporators generally, the distance between the condensation surface, which is a cold surface, and the evaporation surface, which is a hot surface, significantly affects the efficiency of the evaporator. The short-path, wiped-film evaporator 10 has a decreased distance between the evaporation surface and the condensation surface due to the internal condenser 16, as compared to wiped-film evaporator 20 having an external condenser 26 that is separated from the evaporation surface by a greater distance. Consequently, short-path, wiped-film evaporator 10 can operate at lower pressures than wiped-film evaporator 20, due to the shorter vapor path in short-path, wiped-film evaporators. For example, short-path, wiped-film evaporators can operate at pressures as low as about 0.001 mbar. This low pressure is not achievable in the wiped-film evaporator 20. By achieving lower pressures, lower process temperatures can also be achieved in short-path, wiped-film evaporators. For example, for many organic materials, each order of magnitude decrease in pressure results in a 25° C. lowering of the boiling temperature.

Accordingly, the higher pressures in wiped-filmed evaporators require that polymers, such as polycyanoacrylate, be heated to higher temperatures than those used in short-path, wiped film evaporators. As stated above, heating polymers to high temperatures is undesirable, because it can produce hot monomers and unwanted byproducts. By operating at lower pressures and temperatures, short-path, wiped-film evaporators at least significantly reduce production of hot monomers and/or undesired byproducts.

In addition, in short-path, wiped-film evaporators, there is a short residence time on heated evaporator surfaces. In addition, the product film is agitated to enhance heat transfer and eliminate hot spots in the evaporator. Consequently, only small amounts of material are exposed to high temperature at any one time. Also, the travel time of substances between the hot surface and the cold surface is reduced in short-path, wiped-film evaporators as compared to wiped-film evaporators, thereby providing a higher process efficiency.

Figure 3:
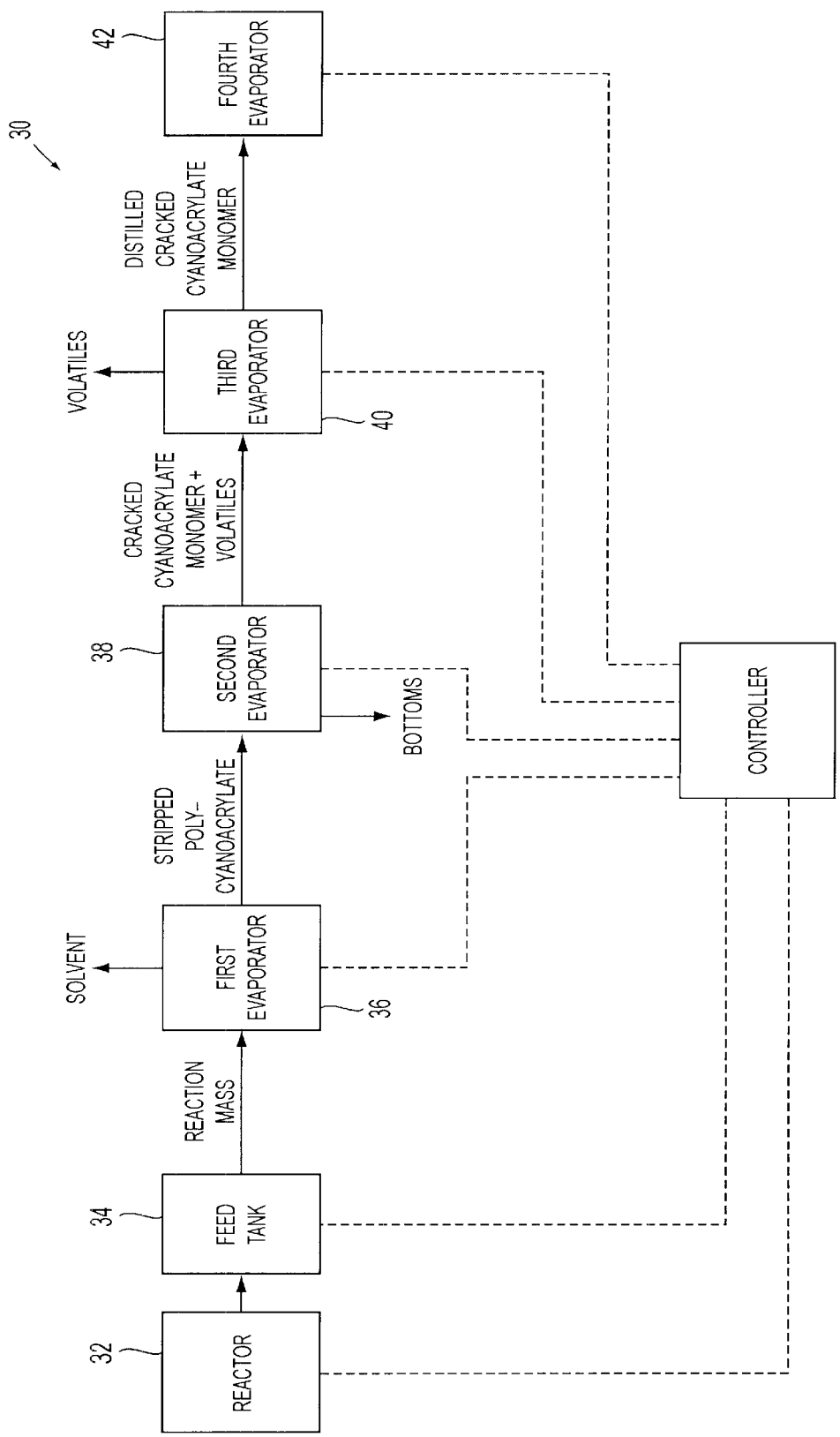
FIG. 3 illustrates an exemplary embodiment of an apparatus for continuously producing cyanoacrylate according to this invention.

FIG. 3 illustrates an exemplary embodiment of an apparatus 30 that can be used in processes for continuously forming cyanoacrylate from polycyanoacrylate according to this invention. Polycyanoacrylate polymer is produced in a reactor 32. The polycyanoacrylate polymer is typically produced by reacting cyanoacetate with a substance such as paraformaldehyde in the presence of a base. The base acts as a catalyst for the reaction between the cyanoacetate and paraformaldehyde. This reaction produces polycyanoacrylate. A solvent such as toluene is used during synthesis to remove water.

The polycyanoacrylate formed in the reactor 32 may be stored in a suitable vessel, such as feed tank 34. As shown, the feed tank 34 is typically in communication with the reactor 32, so that the polycyanoacrylate can be transported directly from the reactor 32 to the feed tank 34.

The reaction mass including the polycyanoacrylate and solvent is fed from the feed tank 34 to a first evaporator 36. The first evaporator 36 is preferably a wiped-film evaporator and, more preferably, a short-path, wiped-film evaporator. The first evaporator 36 is used to perform a stripping step, which removes the solvent from the polycyanoacrylate contained in the reaction mass by evaporating and condensing the solvent.

The first evaporator 36 is operated at an appropriate temperature range, such as from about 40° C. to about 120° C., preferably from about 95° C. to about 115° C., and more preferably from about 100° C. to about 110° C. during the stripping step. The first evaporator 36 is operated at a vacuum pressure of from about 10 torr to about 100 torr, preferably from about 25 torr to about 85 torr, and more preferably from about 40 torr to about 70 torr during the stripping step. Of course, in embodiments, temperatures and pressures outside of these temperature and pressure ranges can alternatively be used, if desired, depending, for example, on the specific polycyanoacrylate and solvent involved.

It is also possible to conduct this process in the presence of an acid gas, such as, for example, $SO_2$.

The solvent is stripped from the reaction mass in the first evaporator 36, preferably in the presence of a suitable radical inhibitor and a dehydrating agent. Preferred radical inhibitors include, but are not limited to, hydroquinone (HQ), butylated hydroxy anisole (BHA), $CuCl_2$ and butylated hydroxy toluene (BHT). Preferred dehydrating agents include, but are not limited to, polyphosphoric acid (PPA), $P_2O_5$, boric acid and mixtures thereof. The solvent stripping preferably removes at least about 99% of the solvent from the reaction mass.

Polycyanoacrylate separated from the reaction mass in the first evaporator 36 is fed to a second evaporator 38 located downstream of second evaporator 38 is preferably a wiped-film evaporator and, more preferably, a short-path, wiped-film evaporator. The second evaporator 38 cracks the polycyanoacrylate to form crude monomer. Volatiles and cracking bottoms are also formed during cracking.

The second evaporator 38 is typically operated at a suitable pressure, such as from about 0.001 torr to about 5 torr, preferably from about 0.001 torr to about 2 torr, and more preferably from about 0.001 torr to about 0.5 torr during the cracking step. The reduced pressure used to crack the polycyanoacrylate allows a corresponding lower temperature also to be used during cracking. For example, the temperature in the second evaporator 38 during the cracking step may be from about 160° C. to about 250° C., preferably from about 175° C. to about 240° C., and more preferably from about 190° C. to about 240° C. Of course, in embodiments, temperatures and pressures outside of these temperature and pressure ranges can alternatively be used, if desired, depending on the polycyanoacrylate being cracked.

The reduced pressure used to crack the polycyanoacrylate in the second evaporator 38 is further advantageous in that it reduces the cracking time during the cracking step as compared to conventional polycyanoacrylate cracking processes that utilize evaporators that operate at higher pressures.

By using reduced cracking pressures, temperatures and times in the second evaporator 38, as compared to the cracking pressures, temperatures and times that are used in known cracking processes that utilize wiped-film evaporators, as well as other types of evaporators, the formation of hot monomer and undesired reaction byproducts can be avoided in the cracking step in the second evaporator 38. Consequently, in embodiments of this invention, it is not necessary to separate such undesired reaction byproducts from the crude monomer that results from cracking the polycyanoacrylate in the second evaporator 38. As a result, processes and apparatus according to this invention can reduce process times and costs, as compared to known processes that utilize other types of evaporators.

Furthermore, the crude monomer that is produced by cracking the polycyanoacrylate in the second evaporator 38 at the reduced cracking temperatures and pressures has enhanced stability.

Cracking bottoms, including uncracked polycyanoacrylate, resulting from the cracking step are preferably removed from the second evaporator 38.

The crude monomer produced by cracking is then distilled to purify the crude monomer. The crude monomer can be distilled using one or more suitable evaporators, to purify the monomer to a desired purity level.

In embodiments, crude monomer is fed from the second evaporator 38 to a third evaporator 40 located downstream of the second evaporator 38. The third evaporator 40 is preferably a wiped-film evaporator and, more preferably, a short-path, wiped film evaporator. In such preferred embodiments, the wiped-film, or short-path, wiped-film, third evaporator 40 can be operated at reduced pressures and temperatures.

In the third evaporator 40, the crude monomer is distilled to extract volatiles from the crude monomer. In this distillation step, in embodiments that utilize a wiped-film evaporator, or a short-path, wiped film evaporator, for the third evaporator 40, the third evaporator 40 may operate at a suitable temperature, such as from about 45° C. to about 110° C., preferably from about 70° C. to about 100° C., and more preferably from about 70° C. to about 90° C. In such embodiments, the third evaporator 40 may be operated at a suitable pressure, such as a vacuum pressure from about 0.1 torr to about 1.6 torr, preferably from about 0.2 torr to about 1.0 torr, and more preferably from about 0.2 torr to about 0.8 torr. Of course, in embodiments, temperatures and pressures outside of these temperature and pressure ranges can alternatively be used, if desired.

Depending on the size of the evaporator, different production rates of the once-distilled monomer can be achieved.

In embodiments of processes according to this invention, distilled crude monomer that has been distilled in the third evaporator 40 is preferably subjected to a second distilling step to further purify the cyanoacrylate monomer. The second distilling step can be performed in the third evaporator 40 or in a fourth evaporator 42. In embodiments, distilled crude monomer is fed from the third evaporator 40 to the fourth evaporator 42 located downstream of the third evaporator 40. The fourth evaporator 42 is preferably a wiped-film evaporator and, more preferably, a short-path, wiped-film evaporator. In such embodiments, the wiped-film, or short-path, wiped-film, fourth evaporator 42 may operate at reduced pressures and temperatures. The fourth evaporator 42 distills the cracked cyanoacrylate monomer a second time to remove undesired substances, such as uncracked polymer and cyanoglutarate, to form a purified monomer product.

In embodiments that utilize a wiped-film evaporator, or a short-path, wiped film, evaporator for the fourth evaporator 42, the fourth evaporator 42 may be operated at a suitable temperature, such as from about 70° C. to about 100° C., preferably from about 75° C. to about 95° C., and more preferably from about 75° C. to about 90° C. The fourth evaporator 42 may be operated at a suitable pressure, such as a vacuum pressure of from about 0.01 torr to about 1.0 torr, preferably from about 0.1 torr to about 0.85 torr, and more preferably from about 0.1 to about 0.5 torr.

Of course, in embodiments, temperatures and pressures outside of these temperature and pressure ranges can alternatively be used, if desired. Low temperatures used in the second distillation step of the cyanoacrylate monomer reduce the heat exposure of the monomer, which thus improves the stability of the purified monomer product. Consequently, the shelf life of the purified monomer is enhanced.

As shown in FIG. 3, the apparatus can optionally include a controller 44 that automatically controls the operating conditions of one or more of the reactor 32, feed tank 34 and first, second, third and fourth evaporators 36, 38, 40 and 42, respectively. Preferably, the controller 44 controls at least the first, second, third and fourth evaporators 36, 38, 40 and 42, respectively. The controller 44 can enable processes according to this invention to be fully automated.

Figure 4:
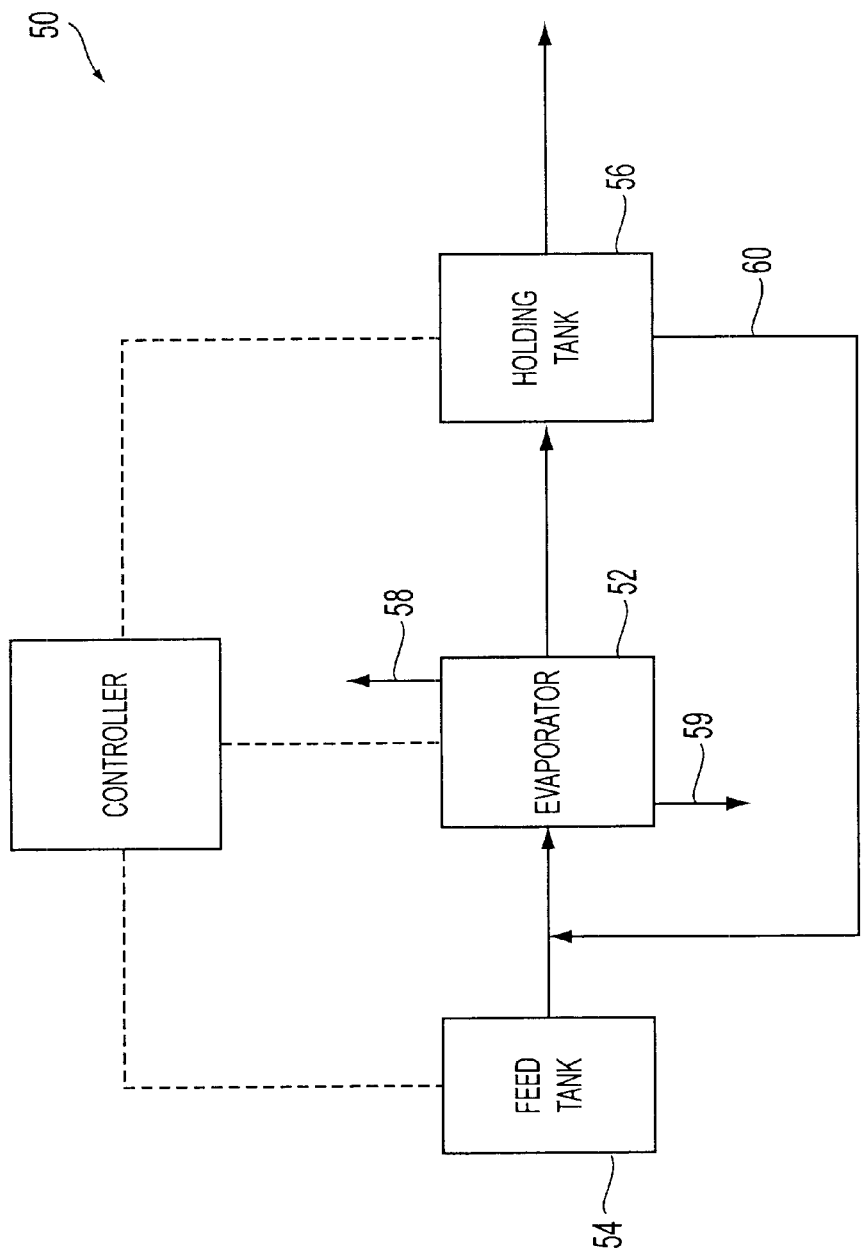
FIG. 4 illustrates another exemplary embodiment of an apparatus for producing cyanoacrylate according to this invention.

This invention also provides processes and apparatus for producing cyanoacrylate in fewer evaporators. For example, two or more of the first, second, third and fourth evaporators discussed above can be the same evaporator. Referring to FIG. 4, in exemplary embodiments of such processes and apparatus 50 two or more, or even all, of the steps of solvent stripping, polymer cracking and monomer distilling are performed in the same evaporator 52. In such embodiments, the evaporator 52 is preferably a wiped-film evaporator and, more preferably, a short-path, wiped-film evaporator. Process conditions utilized in each of the steps in the single wiped-film evaporator, or short-path, wiped-film evaporator, can be the same as the above-describe process conditions that are utilized in processes and apparatus according to this invention that utilize multiple wiped-film evaporators, or multiple short-path, wiped-film evaporators.

In the apparatus 50 a feed tank 54 contains a supply of a reaction mass comprising polycyanoacrylate and solvent that has been produced in a reactor. The reaction mass is subjected to the steps of solvent stripping, polymer cracking and monomer distilling in the evaporator 52. The apparatus preferably also includes a holding container 56 downstream of the evaporator 52 to temporarily hold material that has been formed in the evaporator 52 before this material is re-introduced into the evaporator 52 for subsequent processing.

In embodiments, solvent is stripped from polycyanoacrylate in the evaporator 52 and the stripped polycyanoacrylate is then fed from the evaporator 52 to the holding tank 56 Stripped solvent is removed from the evaporator 52 as indicated at 58 in FIG. 4.

The stripped polycyanoacrylate is then returned to the evaporator 52 via the return passage 60. The stripped polycyanoacrylate is then subjected to cracking in the evaporator 52 to form cracked cyanoacrylate monomer, bottoms and volatile substances. The cracked cyanoacrylate monomer and volatiles are fed to the holding tank 56 The bottoms are removed from the evaporator as indicated at 59.

Next, cracked cyanoacrylate monomer is returned from the holding tank 56 to the evaporator 52 via the return passage 60. The cracked cyanoacrylate monomer is then subjected to one or more distilling step(s), to remove the volatile substances as at 58 and purify the cyanoacrylate monomer. In embodiments in which the cyanoacrylate is distilled more than once, the cyanoacrylate monomer is fed from the evaporator 52 to the holding tank 56 and then returned to the evaporator 52 for subsequent distilling of the distilled cyanoacrylate monomer. As stated above, cyanoacrylate monomer can be distilled twice in the evaporator 52 to produce purified cyanoacrylate monomer.

Processes according to this invention that utilize a single wiped-film evaporator, or a short-path, wiped-film evaporator, are advantageous, for example, when only a single wiped-film or short-path, wiped film evaporator is available for performing the cyanoacrylate production process, or where process space is limited. In addition, these processes are also advantageous for making small amounts of cyanoacrylate.

Processes for producing cyanoacrylates according to this invention can produce alkyl α-cyanoacrylates. Such monomers are known in the art and have the formula:

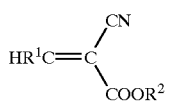 (I)

wherein $R^1$ is hydrogen and $R^2$ is a hydrocarbyl or substituted hydrocarbyl group; a group having the formula —$R^3$—O—$R^4$—O—$R^5$ or the formula —$R^4$—O—$R^5$, wherein $R^3$ is a 1,2-alkylene group having 2–4 carbon atoms, $R^4$ is an alkylene group having 2–4 carbon atoms, and $R^5$ is an alkyl group having 1–6 carbon atoms; or a group of the formula:

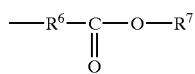 (II)

wherein $R^6$ is —$(CH_2)_n$—,

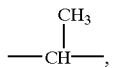

or —$(CH_3)_2$—, wherein n is 1–10, preferably 1–5 carbon atoms, and $R^7$ is an organic radical.

Examples of suitable hydrocarbyl and substituted hydrocarbyl groups include straight chain or branched chain alkyl groups having 1–16 carbon atoms; straight chain or branched chain $C_1$–$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^7$ may be substituted or unsubstituted and may be straight chain, branched or cyclic, saturated, unsaturated or aromatic. Examples of such organic moieties include $C_1$–$C_8$ alkyl moieties, $C_2$–$C_8$ alkenyl moieties, $C_2$–$C_8$ alkynyl moieties, $C_3$–$C_{12}$ cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 6 carbon atoms.

In the cyanoacrylate monomer of formula (I), $R^2$ is preferably an alkyl group having 1–10 carbon atoms or a group having the formula —$AOR^8$, wherein A is a divalent straight or branched chain alkylene or oxyalkylene moiety having 2–8 carbon atoms, and $R^8$ is a straight or branched alkyl moiety having 1–8 carbon atoms.

Examples of groups represented by the formula —$AOR^8$ include 1-methoxy-2-propyl, 2-butoxy ethyl, isopropoxy ethyl, 2-methoxy ethyl, and 2-ethoxy ethyl.

Preferred α-cyanoacrylate monomers used in this invention include 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

In addition, processes and apparatus according to this invention can also produce other types of cyanoacrylates, such as those described in the patents and patent applications incorporated herein by reference.

Processes according to this invention can produce cyanoacrylate monomers that have high purity and contain few impurities. These monomers can be utilized for medical purposes. Monomers utilized for industrial purposes need not always be as pure as those for medical purposes, but can also be produced by processes and apparatus of the invention.

The purified cyanoacrylate monomers produced by processes according to this invention can be applied to substrates in any suitable manner. For example, polymerizable 1,1-disubstituted ethylene monomers, and adhesive compositions comprising such monomers, can be applied to substrates, and particularly in medical applications, as described, for example, in U.S. Pat. Nos. 5,624,669 and 5,928,611 to Leung et al. and U.S. Pat. No. 5,981,621 to Clark et al., and U.S. patent application Ser. No. 08/714,288 to Clark et al. and Ser. No. 09/471,392 to Narang et al., each of which is incorporated herein by reference in its entirety.

As stated above, this invention also provides processes and apparatus for continuously producing cyanoacetate. The cyanoacetate produced by these processes can then be used to produce polycyanoacrylate, which is cracked to form cyanoacrylate monomer by the above-described exemplary embodiments, or alternatively can be stored, shipped and/or used in other processes.

Embodiments of processes for producing cyanoacetate according to this invention comprise synthesizing cyanoacetate and then purifying the cyanoacetate. The synthesizing and purifying steps are preferably both performed in one or more wiped-film evaporators, and preferably in one or more short-path, wiped-film evaporators, so that reduced synthesizing and purifying temperatures and pressures can be used. These steps can be performed in either the same wiped-film evaporator, or alternatively in different wiped-film evaporators.

In embodiments of processes for producing cyanoacetate according to this invention, a first cyanoacetate is reacted with a suitable compound by transesterification, or ester interchange, to form a second cyanoacetate. This reaction is conducted in a wiped-film evaporator. The second cyanoacetate is then purified, preferably in a wiped-film evaporator. Processes for forming cyanoacetate by transesterification are discussed in incorporated U.S. Pat. No. 5,624,669 to Leung et al.

In exemplary embodiments, the first cyanoacetate can be a lower homologue cyanoacetate and the second cyanoacetate can be a higher homologue cyanoacetate. For example, the first cyanoacetate can be ethyl or methyl cyanoacetate and the second cyanoacetate can be 2-octyl cyanoacetate.

Figure 5:
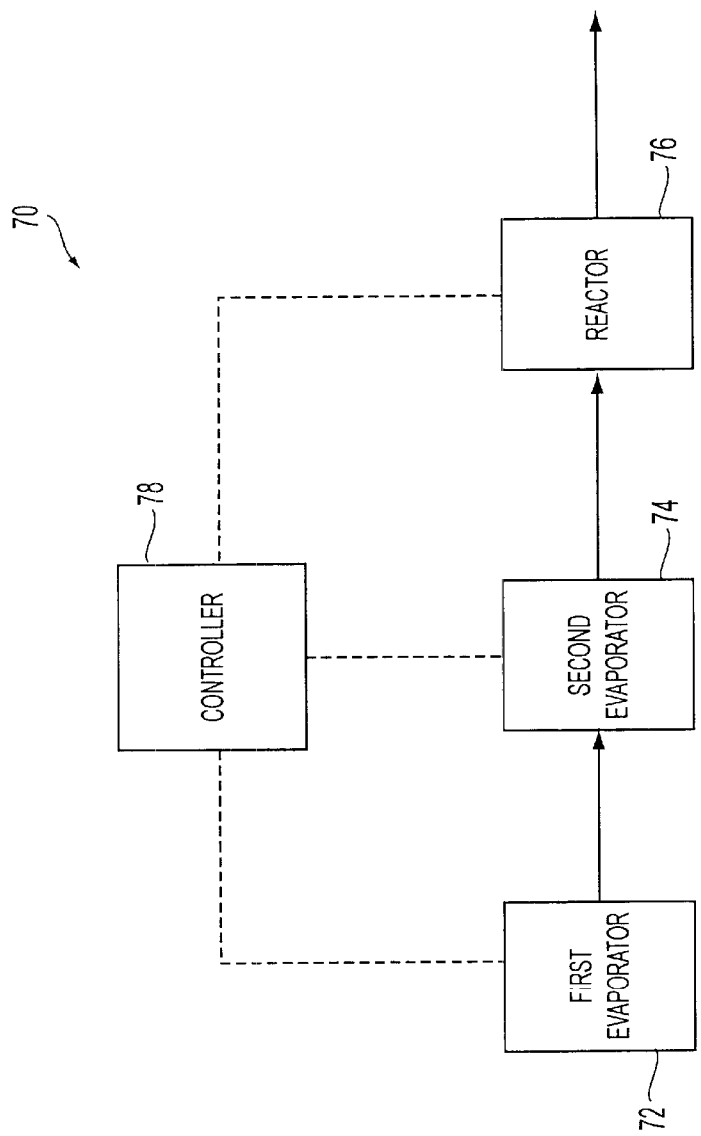
FIG. 5 illustrates an exemplary embodiment of an apparatus for producing cyanoacetate according to this invention.

Referring to FIG. 5, an exemplary embodiment of an apparatus 70 for producing cyanoacetate in a continuous process comprises a first evaporator 72 and a second evaporator 74 downstream of the first evaporator 72. A reactor 76 for forming polycyanoacrylate is shown downstream of the second evaporator 74. A controller 78 can optionally be used to control cyanoacetate production.

The first evaporator 72 used for transesterification can have a suitable operating temperature, such as from about 100° C. to about 250° C. during the synthesizing step, preferably a temperature of from about 120° C. to about 210° C., and more preferably a temperature of from about 140° C. to about 175° C. The operating pressure of the first evaporator 72 during the synthesizing step is preferably about atmospheric pressure. Of course, in embodiments, temperatures and pressures outside of these temperature and pressure ranges can alternatively be selected by those of ordinary skill in the art in light of this disclosure.

The second evaporator 74 used in embodiments for the purifying step can have a suitable operating temperature, such as from about 75° C. to about 105° C., preferably from about 80° C. to about 100° C., and more preferably from about 85° C. to about 95° C. The second evaporator 74 can have a suitable operating pressure, such as from about 0.5 torr to about 10 torr during the step of purifying the first cyanoacetate. Of course, in embodiments, temperatures and pressures outside of these temperature and pressure ranges can be selected by those of ordinary skill in the art in light of this disclosure.

In embodiments of processes for producing cyanoacetate according to this invention, cyanoacetate can be produced by the esterification of cyanoacetic acid. For example, cyanoacetic acid can be mixed with an excess amount of alcohol, such a 2-octanol, in the presence of a strong acid, such as sulfuric acid, p-toluenesulfonic acid, methanesulfonic acid and trifluoroacetic acid, and fed into a wiped-film evaporator set to a temperature below the boiling point of the alcohol. An ester is produced in the wiped-film evaporator. Preferably, the ester has a high boiling point.

In embodiments of this invention, purified cyanoacetate product that is formed by the continuous cyanoacetate processes can be used to form polycyanoacrylate in the reactor 76 in a continuous process. As stated, the polycyanoacrylate that is continuously produced by these processes can be used in the above-described continuous processes for forming cyanoacrylate according to this invention.

Particularly, the purified cyanoacetate can be reacted with a suitable substance in the presence of a suitable catalyst in reactor 76 to form polycyanoacrylate. For example, the cyanoacetate can be reacted with formaldehyde or a functional equivalent, such as the polymeric form paraformaldehyde or formaline, to form polycyanoacrylate. Processes for forming polycyanoacrylate by reacting cyanoacetate with a substance, such as paraformaldehyde, are discussed in U.S. patent application Ser. No. 09/443,298 to Malofsky et al., which is incorporated herein by reference in its entirety.

The catalyst can be any suitable basic material. Suitable basic substances for use as the catalyst include, for example, piperidine, piperidine hydrogen chloride, sodium bicarbonate and triethylamine.

The catalyst is dissolved in any suitable solvent. For example, a suitable solvent is toluene.

The reaction of cyanoacetate with paraformaldehyde in the presence of the catalyst produces polycyanoacrylate, formaldehyde and solvent. In order to produce cyanoacrylate monomer, the solvent is stripped off, and polycyanoacrylate polymer is cracked, preferably as described above. Conventional processes for forming polycyanoacrylate from cyanoacetate are described, for example, in U.S. Pat. Nos. 2,467,927 and 2,721,858, which are each incorporated herein by reference in their entirety.

The following examples illustrate specific embodiments of the present invention. One skilled in the art will recognize that process conditions may be adjusted to achieve specific process results.

EXAMPLES

The following examples are performed in an apparatus as shown in FIG. 4. In Example 1, a reaction mass of polycyanoacrylate and toluene produced during synthesis in a reactor are fed into a short-path wiped-film evaporator operated at the process conditions shown in TABLE 1 below. The wiped-film evaporator separates the toluene (distillate) from the reaction mass, producing a polycyanoacrylate residue.

The polycyanoacrylate residue is then subjected to the process conditions shown in TABLE 1 in the same wiped-film evaporator to crack the polycyanoacrylate and form a distillate comprising crude cracked cyanoacrylate monomer and uncracked polycyanoacrylate residue.

Next, the crude cyanoacrylate monomer is subjected to two distilling steps in the wiped-film evaporator, in order to purify the crude cyanoacrylate monomer and produce a purified cyanoacrylate monomer. The process conditions for the first and second distillation steps are shown in TABLE 1. The first distilling step distills the crude cyanoacrylate monomer to remove low boiling point substances, such as one or more of octene, octanol, propionate and acetate, to form a more concentrated cyanoacrylate monomer and typically also other substances, such as dicyanoglutarate.

The once-distilled cyanoacrylate monomer and high boilers are then subjected to the second distillation step. In this step, the twice-distilled pure cyanoacrylate monomer is separated from the residue.

TABLE 1

| Example No. 1 | |
|---|---|
| Solvent Stripping | |
| Feed Rate | ~170 gm/hr |
| Feed Temp. | ~70° C. |
| Evaporator Temp. | 100° C. |
| Wiper Speed | 450 rpm |
| Pressure (mmHg) | 20 |
| Condenser Temp. | −20° C. |
| Residue Temp. | 90° C. |
| Residue (%) | ~82 |
| Distillate (%) | ~17 |
| Trap (%) | ~1 |
| Polymer Cracking | |
| Feed Rate | ~90 gm/hr |
| Feed Temp. | 120° C. |
| Wiper Speed | 450 rpm |
| Evaporator Temp. | 238° C. |
| Pressure (mmHg) | 0.041 |
| Condenser Temp. | −20° C. |
| Residue (%) | 38.1 |
| Distillate (%) | 56.3 |
| Trap (%) | 5.6 |
| First Distillation Crude Source | |
| Feed Rate | ~145 gm/hr |
| Evaporator Temp. | 75° C. |

TABLE 1-continued

Example No. 1

| | |
|---|---|
| Wiper Speed | 400 rpm |
| Pressure (mmHg) | 0.314 |
| Condenser Temp. | 5° C. |
| Residue (%) | 80.4 |
| Distillate (%) | 19.6 |
| Trap (%) | 0 |
| Second Distillation | |
| Feed Rate | ~160 gm/hr |
| Evaporator Temp. | 90° C. |
| Wiper Speed | 400 rpm |
| Pressure (mmHg) | 0.18 |
| Condenser Temp. | 5° C. |
| Residue (%) | 86.3 |
| Distillate (%) | 13.7 |
| Trap (%) | 0.0 |

Examples 2–7 are conducted to further demonstrate the formation of crude cyanoacrylate monomer by the performance of a solvent stripping step and a polymer cracking step, in accordance with this invention. The process conditions used for the solvent stripping step and the polymer cracking step are shown in TABLE 2 below. The distillate is then analyzed for Example Nos. 1–4, 6 and 7.

TABLE 2

| Example No. | 2 | 3 | 4 | 5 | 6 | 7 |
|---|---|---|---|---|---|---|
| Solvent Stripping | | | | | | |
| Feed Rate (gm/hr) | ~140 | ~250 | ~250 | ~330 | ~350 | ~250 |
| Feed Temp. | ambient | ambient | ambient | ambient | ambient | ~70°C. |
| Evaporator Temp. (° C.) | 100 | 100 | 100 | 100 | 100 | 100 |
| Wiper Speed (rpm) | 400 | 400 | 400–500 | 500 | 450 | 450 |
| Pressure (mmHg) | 10 | 10–12 | 10–14 | 10 | 12 | 15–20 |
| Condenser Temp. (° C.) | 5 | 5 | 5 | −10 | −10 | −20 |
| Residue Temp. (° C.) | 90 | 90 | 90 | 90 | 90 | 90 |
| Residue (%) | ~81 | ~81 | ~85 | ~82 | ~80 | ~82 |
| Distillate (%) | ~3 | ~2 | ~4 | ~11 | ~18 | ~12 |
| Trap (%) | ~16 | ~17 | ~11 | ~7 | ~2 | ~5 |
| Polymer Cracking | | | | | | |
| Feed Rate (gm/hr) | ~60 | ~80 | ~40 | ~100 | ~125 | ~80 |
| Feed Temp. (° C.) | 90 | 110 | 110 | 120 | 120 | 120 |
| Wiper Speed (rpm) | 400 | 400–500 | 500 | 500 | 500 | 450 |
| Evaporator Temp. (° C.) | 240 | 220–230 | 235–238 | 238 | 235 | 235–237 |
| Pressure (mmHg) | 0.1* | 0.07* | 0.061 | 0.051 | 0.065 | 0.2–0.3 |
| Condenser Temp. (° C.) | 5 | 5 | 5 | −10 | −20 | −20 |
| Residue (%) | NA** | 68.6 | 19.7 | 1.1 | 4.8 | 65.3 |
| Distillate (%) | 86.3 | 27.6 | 73.7 | 93.8 | 92.0 | 30.0 |
| Trap (%) | NA | 3.8 | 6.6 | 5.1 | 3.2 | 4.7 |
| Distillate Data | | | | | | |
| Octene (ppm) | 2,503 | 7,994 | 7,095 | NA | 6,026 | 4,485 |
| Octanol (ppm) | 13,375 | 24,148 | 17,334 | NA | 15,290 | 21,383 |
| Propionate (%) | NA | 0.61 | 0.7 | NA | None | 0.92 |
| Acetate (%) | NA | 7.58 | 9.42 | NA | 7.18 | 13.32 |
| Acrylate Purity (%) | NA | 85.42 | 81.75 | NA | 90.36 | 76.45 |

*Used pirani vacuum gauge for pressure measurement
**NA = Not Analyzed.

While the invention has been described in conjunction with the specific embodiments described above, it is evident that many alternatives, modifications and variations will be apparent to those skilled in the art. Accordingly, preferred embodiments of the invention as set forth above are intended to be illustrative and not limiting. Various changes can be made without departing from the spirit and scope of the invention.

What is claimed is:

1. A process for continuously producing cyanoacrylate monomer, comprising the steps:

(a) stripping solvent from a reaction mass comprising polycyanoacrylate and solvent in a first wiped-film evaporator to produce stripped polycyanoacrylate;

(b) cracking the stripped polycyanoacrylate to form a cracked cyanoacrylate monomer and residue substances in a second wiped-film evaporator; and (c) distilling the cracked cyanoacrylate monomer to produce a purified cyanoacrylate monomer.

2. The process of claim 1, wherein step (c) comprises:

feeding the cracked cyanoacrylate monomer and residue substances to a third wiped-film evaporator; and distilling the cracked cyanoacrylate monomer and the residue substances in the third wiped-film evaporator to separate the residue substances from the cracked cyanoacrylate monomer.

3. The process of claim 2, wherein distilling the cracked cyanoacrylate further comprises:

feeding the distilled cracked cyanoacrylate monomer to a fourth wiped-film evaporator; and distilling the distilled cracked cyanoacrylate monomer in the fourth wiped-film evaporator to produce a purified cyanoacrylate monomer.

4. The process of claim 3, wherein the first wiped-film evaporator, second wiped-film evaporator, third-wiped film evaporator and fourth wiped-film evaporator are the same wiped-film evaporator.

5. The process of claim 3, wherein the first wiped-film evaporator, second wiped-film evaporator, third wiped-film evaporator and fourth wiped-film evaporator are each a short-path, wiped-film evaporator.

6. The process of claim 2, wherein the first wiped-film evaporator, second wiped-film evaporator and third wiped-film evaporator are the same wiped-film evaporator.

7. The process of claim 2, wherein the first wiped-film evaporator, second wiped-film evaporator and third wiped-film evaporator are each a short-path, wiped-film evaporator.

8. The process of claim 1, wherein the first wiped-film evaporator and the second wiped-film evaporator are the same wiped-film evaporator.

9. The process of claim 1, wherein the first wiped-film evaporator and the second wiped-film evaporator are each a short-path, wiped film evaporator.

10. The process of claim 1, wherein the first wiped-film evaporator is a short-path, wiped-film evaporator.

11. The process of claim 1, wherein the first wiped-film evaporator operates at a temperature of from about 40° C. to about 120° C. and a vacuum pressure of from about 10 torr to about 100 torr during the stripping.

12. The process of claim 1, wherein the second wiped-film evaporator operates at a temperature of from about 160° C. to about 250° C. and a pressure of from about 0.001 torr to about 5 torr during the cracking.

13. The process of claim 1, wherein the solvent is stripped from the reaction mass in the presence of a radical inhibitor and a dehydrating agent in the first wiped-film evaporator.

14. The process of claim 2, wherein the third wiped-film evaporator operates at a temperature of from about 45° C. to about 110° C. and a vacuum pressure of from about 0.1 torr to about 1.6 torr during the distillation of the cracked cyanoacrylate monomer.

15. The process of claim 3, wherein the fourth wiped-film evaporator operates at a temperature of from about 70° C. to about 100° C. and a vacuum pressure of from about 0.01 torr to about 1.0 torr during the distillation of the distilled cracked cyanoacrylate monomer.

16. The process of claim 3, wherein:

the first wiped-film evaporator operates at a temperature of from about 40° C. to about 120° C. and a vacuum pressure of from about 10 torr to about 100 torr during the stripping;

the second wiped-film evaporator operates at a temperature of from about 160° C. to about 250° C. and a pressure of from about 0.001 torr to about 5 torr during the cracking;

the third wiped-film evaporator operates at a temperature of from about 45° C. to about 110° C. and a vacuum pressure of from about 0.1 torr to about 1.6 torr during the distillation of the cracked cyanoacrylate monomer; and the fourth wiped-film evaporator operates at a temperature of from about 70° C. to about 100° C. and a vacuum pressure of from about 0.01 torr to about 1.0 torr during the distillation of the distilled cracked cyanoacrylate monomer.

17. The process of claim 1, wherein the cyanoacrylate monomer is an alkyl α-cyanoacrylate.

18. The process of claim 17, wherein the α-cyanoacrylate monomer is selected from the group consisting of octyl cyanoacrylate, 2-ethylhexyl cyanoacrylate, butyl cyanoacrylate, ethyl cyanoacrylate and methyl cyanoacrylate.

19. The process of claim 18, wherein the α-cyanoacrylate is n-butyl or 2-octyl α-cyanoacrylate.

20. The process of claim 1, further comprising, prior to step (a), forming the polycyanoacrylate of the reaction mass by a process comprising:

continuously making a second cyanoacetate by converting a first cyanoacetate to the second cyanoacetate that is a higher homologue cyanoacetate as compared to the first cyanoacetate; and reacting the second cyanoacetate to form the polycyanoacrylate of the reaction mass.

21. The process of claim 20, wherein the second cyanoacetate is formed by a continuous process, comprising:

synthesizing the second cyanoacetate via a transesterification reaction of the first cyanoacetate in a fifth wiped-film evaporator; and purifying the second cyanoacetate in a sixth wiped-film evaporator.

22. The process of claim 21, wherein the fifth wiped-film evaporator and the sixth wiped-film evaporator are the same wiped-film evaporator.

23. The process of claim 20, wherein the first cyanoacetate is ethyl cyanoacetate or methyl cyanoacetate, and the second cyanoacetate is 2-octyl cyanoacetate.

24. The process of claim 21, wherein the fifth wiped-film evaporator and the sixth wiped-film evaporator are each a short-path, wiped-film evaporator.

25. The process of claim 21, wherein the fifth wiped-film evaporator operates at a temperature of from about 100° C. to about 250° C. during the synthesizing step.

26. The process of claim 25, wherein the fifth wiped-film evaporator operates at a pressure of about atmospheric pressure during the synthesizing step.

27. The process of claim 21, wherein the sixth wiped-film evaporator operates at a temperature of from about 75° C. to about 105° C. and a pressure of about 0.5 torr to about 10 torr during the purifying step.

28. The process of claim 21, wherein:

the fifth wiped-film evaporator operates at a temperature of from about 100° C. to about 200° C. and a pressure of about atmospheric pressure during the synthesizing step; and the sixth wiped-film evaporator operates at a temperature of from about 75° C. to about 105° C. and a pressure of about 0.5 torr to about 10 torr during the purifying step.

* * * * *